United States Patent
Knox-Sigh

Patent Number: 5,520,675
Date of Patent: May 28, 1996

[54] FEMININE HYGIENE PAD

[76] Inventor: Annette Knox-Sigh, 3251 Canton, Detroit, Mich. 48207

[21] Appl. No.: 327,304

[22] Filed: Oct. 21, 1994

[51] Int. Cl.⁶ ..................................................... A61F 13/15
[52] U.S. Cl. ..................... 604/385.1; 604/387; 604/393; 604/400
[58] Field of Search ..................... 604/329, 330, 604/331, 379, 380, 385.1, 386, 387, 393–402

[56] References Cited

U.S. PATENT DOCUMENTS

| | | | |
|---|---|---|---|
| 2,331,355 | 10/1943 | Strongson | 604/385.1 |
| 2,742,903 | 4/1956 | Lightner | 128/290 |
| 2,747,575 | 5/1956 | Mercer | 128/290 |
| 3,115,877 | 12/1963 | Harwood | 128/290 |
| 3,528,422 | 9/1970 | Hodas | 128/290 |
| 3,905,372 | 9/1975 | Denkinger | 128/285 |
| 3,906,952 | 9/1975 | Zamist | 128/290 R |
| 3,983,873 | 10/1976 | Hirschman | 604/385.1 |
| 4,072,151 | 2/1978 | Levine | 128/290 R |
| 4,673,403 | 6/1987 | Lassen et al. | 604/385.1 |
| 4,900,319 | 2/1990 | Richwine | 604/385.1 |
| 5,074,855 | 12/1991 | Rosenbluth et al. | 604/385.1 |
| 5,169,394 | 12/1992 | Jean | 604/385.1 |
| 5,290,262 | 3/1994 | Vukos et al. | 604/385.1 |

FOREIGN PATENT DOCUMENTS

| | | | |
|---|---|---|---|
| 731423 | 4/1966 | Canada | 604/904 |
| 588689 | 5/1947 | United Kingdom | 604/397 |

*Primary Examiner*—Randy C. Shay
*Attorney, Agent, or Firm*—Howard & Howard

[57] ABSTRACT

A unique feminine hygiene pad includes a tail that extends rearwardly from a main portion of the pad to be received within the buttocks of a wearer. The tail insures that there will be no leakage flow rearwardly into the buttocks of the wearer, as has typically occurred with prior art pads. In addition, a positioning point is formed on a main absorbent portion of the pad which properly positions the pad relative to the vagina of a wearer. In this way, it can be assured that the pad is properly positioned, and a minimum sized pad can be utilized.

8 Claims, 2 Drawing Sheets

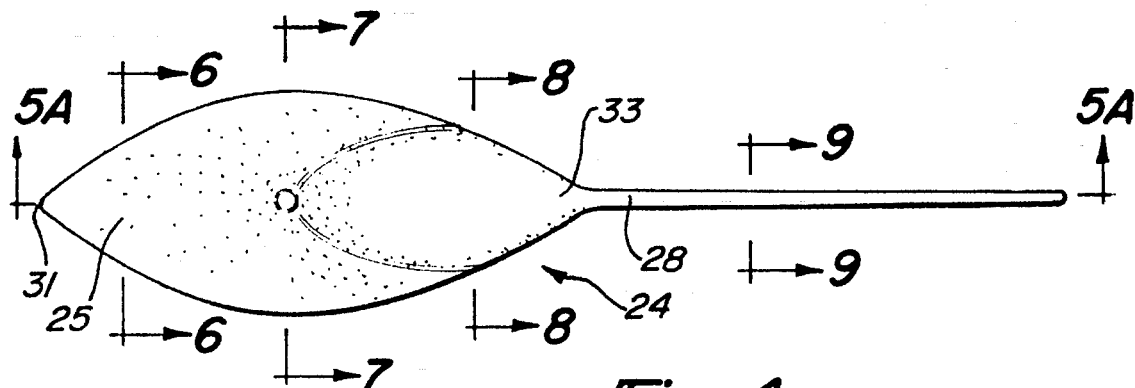
*Fig-4*
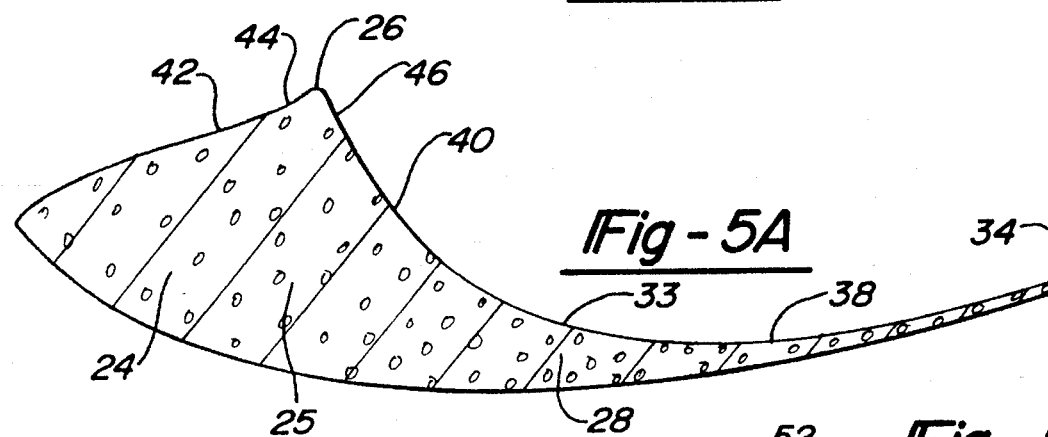
*Fig-5A*
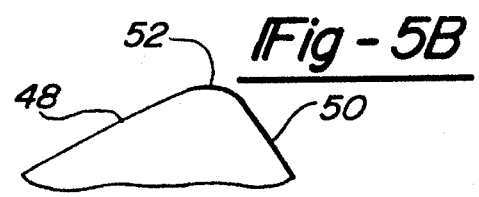
*Fig-5B*
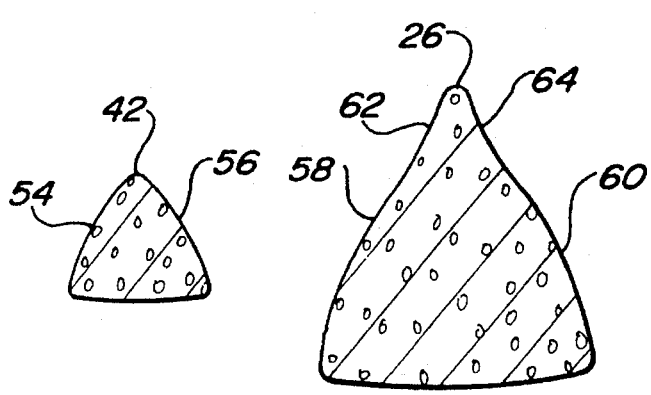
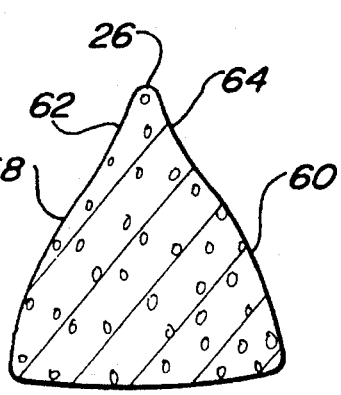
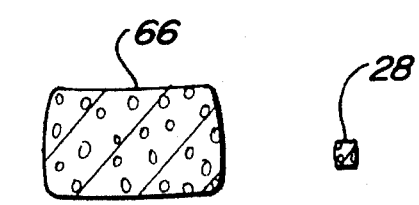
*Fig-6*    *Fig-7*    *Fig-8*    *Fig-9*

FEMININE HYGIENE PAD

BACKGROUND OF THE INVENTION

This Application in general relates to improvements in feminine hygiene pads that provide better absorbency and leak protection and, further, are more comfortable.

The field of feminine hygiene is one in which there have traditionally been trade-offs. On the one hand, it has generally been accepted that the best leak protection is provided by internal devices, such as tampons. However, for many reasons, some users elect to not wear an internal device. This has been more pronounced with the recent realization that toxic shock syndrome can sometimes be related to the use of a tampon product.

For those reasons, many users have desired to wear outer products such as pads. Pads, however, have never successfully provided complete absorbency, or prevention from leakage. One major problem with pads has been that they have been unduly large since they have been positioned adjacent the wearer's clothing, rather than being positioned on the wearer. For that reason, pads have been made of undue width, such that it can be assured they will be properly positioned. Further, the pads have generally not extended rearwardly into the buttocks area. This has resulted in a problem wherein some leakage has escaped between the wearer and the pad and reached the wearer's buttocks area, causing irritation and discomfort.

In general, pads have suffered from a belief by wearers that they are too large, while at the same time, they have not provided sufficient leak protection or absorbency, since it is difficult to properly position them. For those reasons, known feminine hygiene pads have not successfully addressed the problem of providing complete hygienic control to a wearer.

At least one prior art reference has proposed a portion extending slightly rearwardly from a main absorbent portion of the pad to address leakage flow rearwardly into the buttocks of a wearer. This portion has not been combined with other structure to properly position the pad relative to the wearer. Further, this proposed portion would not have extended for sufficient length that it would have been received within the buttocks of a wearer, and thus it would not have provided sufficient leak prevention. Moreover, the portion as described was of such great width that it would not have properly fit between the buttocks of a wearer. It could not have been worn comfortably, nor could it have properly provided its anti-leak function.

SUMMARY OF THE INVENTION

In a disclosed embodiment of this invention, a pad has a relatively thin tail portion extending rearwardly for a length approximately equal to the entire length of the remainder of the pad. This tail is formed of an absorbent material, and fits upwardly within the space between the buttocks of the wearer. The tail prevents leakage traveling into the buttocks, causing discomfort or irritation to the wearer.

In a preferred embodiment of this invention, the tail is formed of a width that is less than one-fifth the width of the remainder of the pad. The tail preferably starts at a location approximately near the perineum of the wearer. The tail is generally curved to conform to the shape of the wearer, such that it will closely overlie the wearer's contours, and provide adequate leak protection.

The remainder of the pad is relatively small when compared to prior art pads. This increases the comfort of the pad. The inventive pad can be relatively small when compared to other pads for two reasons. First, the tail provides insurance against leakage rearwardly of the pad. This allows the pad to be of a reduced area. Secondly, the pad includes a unique contour including a positioning point insuring that the pad is properly positioned relative to the wearer. The unique positioning point is an improvement over prior pads that were positioned adjacent the clothing of the wearer. Those prior pads had to be of sufficient size such that mis-positioning could be overcome. With the inventive positioning point, it is assured that the pad is properly positioned, and thus a minimum size for the pad may be used.

The positioning point also insures the tail successfully achieves its function. It is important that the tail be properly positioned, as it is relatively small. In the absence of the positioning point one could not be as confident the tail will be properly positioned.

In other features of this invention, the main portion of the pad has a unique contour that curves upwardly from forward and rearward positions towards the positioning point. At the same time, the pad curves upwardly from each side of the main portion of the pad, providing both a primary and a secondary absorbent area.

These and other features of the present invention can be best understood from the following specification and drawings, of which the following is a brief description.

BRIEF DESCRIPTION OF THE DRAWINGS

FIG. 4 is a plan view of the inventive pad..

FIG. 5A is a cross-sectional view along line 5—5 as shown in FIG. 4.

FIG. 5B is a cross-sectional view of a portion of the pad illustrated in an alternative embodiment.

FIG. 6 is a cross-sectional view along line 6—6 as shown in FIG. 4.

FIG. 7 is a cross-sectional view along line 7—7 as shown in FIG. 4.

FIG. 8 is a cross-sectional view along line 9—8 as shown in FIG. 4.

FIG. 9 is a cross-sectional view along line 9—9 as shown in FIG. 4.

DETAILED DESCRIPTION OF PREFERRED EMBODIMENT

Figure 1:
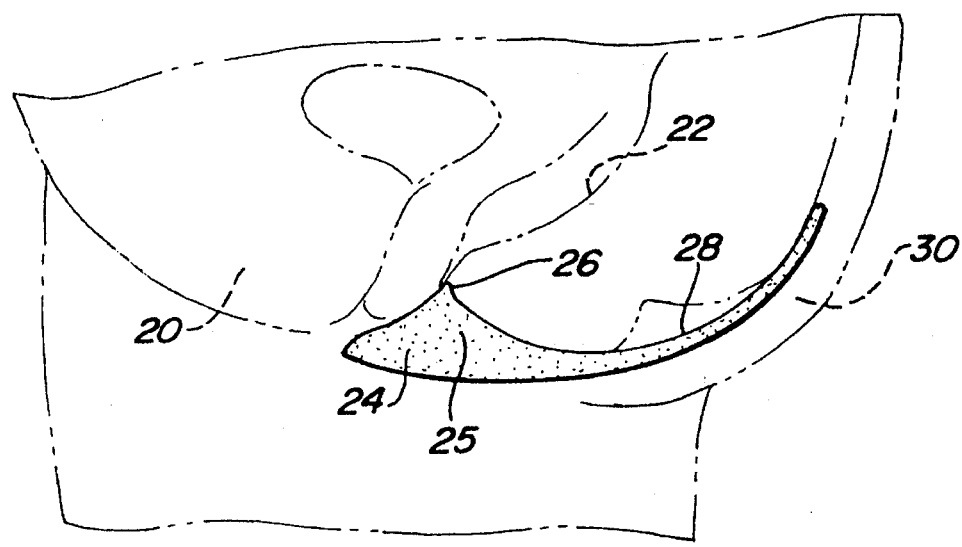
FIG. 1 is a cross-sectional view showing a wearer with the inventive pad.

FIG. 1 is a view of a wearer 20 utilizing the inventive pad. As shown, the inventive pad is positioned adjacent the vagina 22 of the wearer 20. The pad 24 includes a main absorbent portion 25 having a positioning point 26 received within the vagina, properly positioning pad 24 relative to the wearer. Since the positioning point 26 insures the pad 24 will always be properly positioned relative to the wearer, the relatively large size of pads as required by the prior art may be eliminated.

A tail 28 extends from the main portion 25 of pad 24 and upwardly into the crack between the buttocks 30 of the wearer. As shown, tail 28 is formed of absorbent material and is curved to conform to the shape of the wearer's body. The tail closely overlies the wearer's body to prevent leakage flow from causing discomfort or irritation to the wearer in the buttocks area. In use, the tail will not be visible, although it can be seen in this cross-sectional view.

Figure 2:
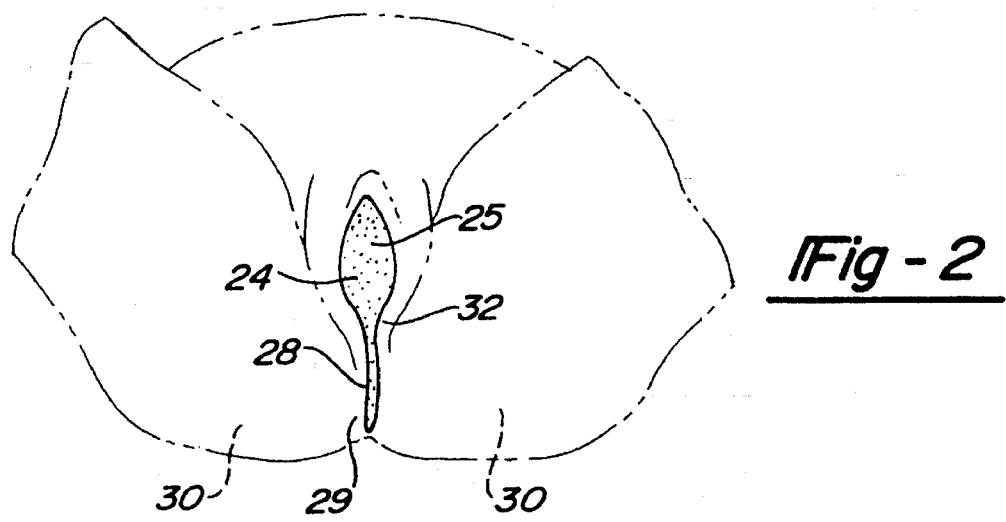
FIG. 2 is a front view of the inventive pad as worn by a wearer.

FIG. 2 is a front view of wearer 20 wearing pad 24. As shown, tail 28 extends rearwardly into the area of the space 29 between the buttocks 30 of the wearer. As will be appreciated, this absorbent tail portion 28 will prevent leakage. Tail 28 is shown beginning adjacent to the perineum 32 of the wearer. The main portion 25 of the pad absorbs the great majority of the flow of the wearer during her menstrual cycle. The tail 28 insures that there is no leakage extending rearwardly from the wearer, as often happens while the wearer is sleeping with prior art pads. As further shown, the pad is of relatively small size, particularly in the width dimension. The pad may thus be more comfortably worn than prior art pads, which were not always properly positioned, and thus needed to be of greater width.

Figure 3:
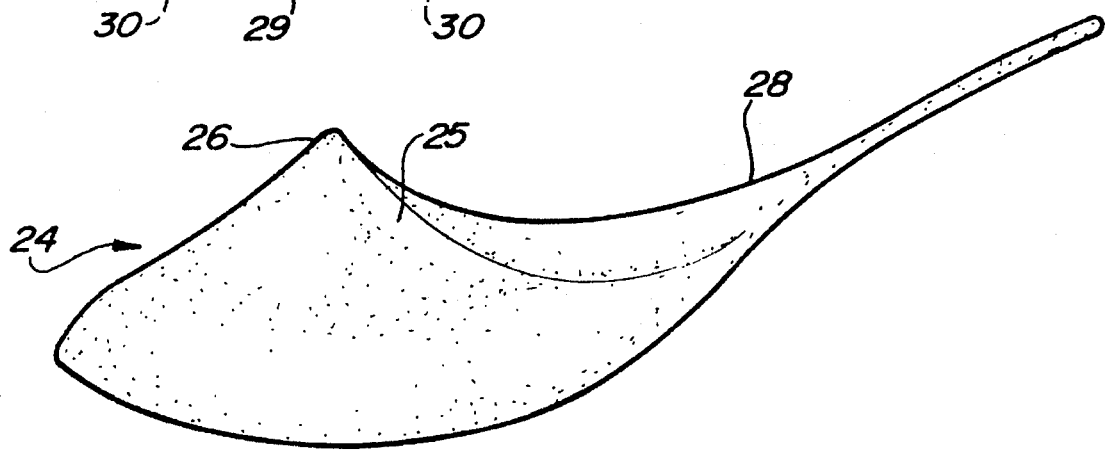
FIG. 3 is a perspective side view of the inventive pad.

FIG. 3 is a perspective view of pad 24, showing main portion 25 and tail 28. As can be seen, positioning point 26 is an uppermost portion of the pad, and the main portion 25 of the pad curves away from positioning point 26 around the entire perimeter of positioning point 26.

As shown in FIG. 4, positioning point 26 is at a location in the approximate center of the main pad portion 25. Tail 28 extends rearwardly for a length which is approximately equal to the length of the remainder of the pad. A length is defined for pad 24 extending from the left to right as shown in FIG. 4. A thickness is defined extending into the plane of the paper of FIG. 4. A width is defined from the top to bottom of the FIG. 4 drawing. As will be appreciated, the thickness in application would be the dimension extending from the contact face of the pad adjacent to the wearer, in a direction away from the wearer. The width is defined as the distance from the right to left of the wearer. The length is defined from a forward position relative to the wearer to a rearward position.

As shown in FIG. 4, the relative width of the tail to the main body portion is quite small. The ratio of the width of the main body portion 25 to the tail 28 is greater than five to one. The length of the tail 28 is preferably on the order of five inches. The drawings in this Application are all drawn to scale, and from this one dimension, the relative dimensions of the other portions of the pad can be appreciated.

As shown in FIG. 5A, tail 28 extends from a tail forward end 33 towards a tail rearward end 34. The contour 38 of tail 28 curves between ends 33 and 34. Further, the tail 28 becomes slightly thinner in the thickness dimension along contour 38. As is clear from FIG. 4, the width of tail 28 does not change between ends 33 and 34.

As further shown in FIG. 5A, a contour 40 of main pad 25 curves upwardly from tail portion 28 towards the positioning point 26. The contour is as shown in FIG. 5A. A forward contour 42 extends upwardly from the forward end of the pad also towards positioning point 26. As shown in FIG. 5A, second contour portions 44 and 46 can extend from contour portions 42 and 40, respectively, such that positioning point 26 is a true point, distinct from the contour portions 40 and 42 leading towards point 26. Note that the contour portions 44 and 46 both extend at a greater slope than the respective contour portions 42 and 40.

As shown in FIG. 5B, as an alternative to the construction of positioning point 26 as shown in FIG. 5A, the contour portions 48 and 50 may extend to a relatively flat positioning point 52. In this embodiment, the positioning point 52 is essentially formed without the second higher sloped portions 44 and 46. The positioning point 52 would not fit as high up into the vagina as with the embodiment shown in FIG. 5A, however, it is still anticipated that the point 52 will provide sufficient positioning and absorbency control.

Also with regard to FIG. 4, the pad extends from a forwardmost portion 31 of the main pad body 25 toward a rearwardmost portion 33, which is also equal to the forwardmost portion of tail 28. The contour of the main portion of the pad 25 in the width direction extends from point 31 curving gradually outwardly to a main width approximately at the location of positioning point 26, and then begins to curve inwardly again until reaching the point 33. Thus, the size of main pad portion 25 is kept at a minimum. This benefit is largely achieved due to the use of the positioning point 26.

As further can be clear from FIG. 5A, there is a main pad portion adjacent to positioning point 26 that will provide the bulk of the absorbency. The lower portion of main pad 25 along contour 40, however provides a secondary absorbency area. When compared to FIG. 1, it can be seen that a good deal of the secondary absorbency layer is outward of the wearer's body, however, it is still positioned to absorb a good deal of leakage flow.

As shown in FIG. 6, main pad body 25 includes contours 54 and 46 curving upwardly to provide increased thickness between the two side ends.

FIG. 7 shows contour portions 58 and 60, leading to secondary contour portions 62 and 64, again of greater slope than their respective contour portions 58 and 60, and leading to positioning point 26. Secondary contour 62 and 64 result in positioning point 26 being a point extending at a great slope relative to the remainder of the main pad body 25.

With either positioning point 26 or 52, the pad curves away from the positioning point along the entirety of the perimeter of the positioning point in both the width and thickness dimensions as one moves along the length of the pad. Since Applicant has invented the positioning point which properly positions the main pad 25, the inventive pad is able to reduce the amount of pad material away from the positioning point, and still achieve sufficient absorbency.

FIG. 8 is a cross-sectional view through the portion of the main pad body 25 which is being defined as the "secondary" absorbency area. As shown, the top contour 66 is relatively flat along the side-to-side dimension.

FIG. 9 shows a portion of the tail 28, which is relatively small in both the thickness and width dimensions. As can be seen from the various drawings, the width of tail 28 relative to main pad portion 25 is less than one-fifth of the main pad portion 25. Moreover, the pad moves to thickness that are also less than one-fifth the thickness of the main pad portion at the location of the positioning point. In fact, comparing the thickness of FIG. 9 to the thickness evidenced in, for example, FIG. 7, the ratio is actually much greater.

The inventive pad may be formed of known pad materials. Preferably, the area adjacent to the positioning point, and the primary absorbency area in the neighborhood of the positioning point is formed of a first material of relatively great absorbency. The secondary absorbency area, surrounding the first absorbency area, and also including the tail 28, is preferably formed of a material that is not as absorbent as the primary absorbency area, but still absorbent material.

A preferred embodiment of this invention has been disclosed, however, a worker of ordinary skill in the art would recognize that certain modifications may come within the scope of this invention. For that reason, the following claims should be studied in order to determine the true scope and content of this invention.

I claim:

1. A feminine hygiene pad comprising:

a main absorbency area having a first face formed of absorbent material for contact with a wearer's body and an opposing second face for facing toward an undergarment of a wearer, a width being defined as a side-to-side dimension of the pad, a thickness being defined as the dimension of the pad from the first face to the second face and a length being defined as the distance from a front end to a rear end of the pad, said pad including a wide and thick main portion to be worn adjacent to the vagina of a wearer; and said pad further including a tail of absorbent material, said tail being relatively small in the dimension of width and thickness compared to said main portion, said tail being long in the length dimension, and said tail extending rearwardly from the main portion of said pad, and being configured to be received between the buttocks of the wearer to prevent leakage and;

a positioning point formed on said first face of said main portion, said first face of the pad curving around the entire perimeter of said positioning point from a pointed extremity of said positioning point toward said second face so that the pad is thickest at the positioning point and gets progressively thinner in every direction extending away from the positioning point.

2. A pad as recited in claim 1, wherein said tail extends for a distance approximately equal to the length of the main portion of the pad.

3. A pad as recited in claim 1, wherein said tail extends for approximately five inches, and begins at a location which is configured to be received near the perineum of the wearer.

4. A pad as recited in claim 2, wherein said tail is curved along its length in the direction of the thickness to conform to the contour of a wearer's body.

5. A pad as recited in claim 4, wherein the relative width and thickness of the main portion of the pad relative to the tail are both greater than five-to-one at the widest and thickest portions of the main portion of the pad.

6. A pad as recited in claim 1, wherein said positioning point curves at a greater slope than the portions leading towards said positioning point.

7. A pad as recited in claim 4, wherein said pad has a forwardmost pointed end defined in the length direction, curves gradually outwardly to achieve the width of the main portion at a portion approximately aligned in the length direction with said positioning point, and then curves gradually back to being of the width of the tail at the position where the tail begins.

8. A feminine hygiene pad comprising:

a main absorbent portion including a positioning point to be received in the vagina of a wearer to properly position the pad relative to the wearer, said main pad portion including a first face for being positioned adjacent to a wearer and an opposing second face for facing an undergarment of a wearer, a thickness being defined as the dimension of the pad extending from the first face to the second face, the width of the pad being defined as a side-to-side dimension and the length of the pad being described as a forward-to-rearward dimension, said first face of said main portion of said pad curving and towards said positioning point in both the width and length direction such that said positioning point is an outer most portion of said main portion, and said first face of said pad curves away from said positioning point and toward said second face around the entire parameter of said positioning point such that the pad is thickest at the positioning point and gets progressively thinner in every direction extending away from the positioning point; and a tail formed of absorbent material extending rearwardly from said main portion of said pad, said tail being configured to be received within the buttocks of a wearer preventing leakage and said tail being relatively small in width and thickness compared to said main portion.

* * * * *